United States Patent [19]

Kildal et al.

[11] Patent Number: 5,329,686
[45] Date of Patent: Jul. 19, 1994

[54] SLIDE FRAME AND MANUFACTURING PROCESS

[75] Inventors: Maurice A. Kildal, Webster, N.Y.; Frank A. Richardson, Charlotte, N.C.; Brendan N. Leather; Claude E. Monsees, both of Fort Mill, S.C.

[73] Assignee: Eastman Kodak Company, Rochester, N.Y.

[21] Appl. No.: 810,942

[22] Filed: Dec. 19, 1991

[51] Int. Cl.⁵ .............................................. B23P 11/00
[52] U.S. Cl. ........................................ 29/450; 29/509; 264/249
[58] Field of Search ................. 29/449, 450, 509, 451; 264/249; 422/56, 57, 58, 104

[56] References Cited

U.S. PATENT DOCUMENTS

| | | | |
|---|---|---|---|
| 2,431,238 | 11/1947 | Friedman | 264/249 |
| 2,715,169 | 8/1955 | High | 29/509 |
| 3,214,811 | 11/1965 | Adinolfi | 29/450 X |
| 3,287,854 | 11/1966 | Dasovic et al. | 29/450 X |
| 4,087,897 | 5/1978 | Scholefield | 29/509 |
| 4,095,327 | 6/1978 | Hartmann | 29/509 |
| 4,169,751 | 10/1979 | Yen | |
| 4,440,301 | 4/1984 | Intengan | 422/57 X |
| 4,564,503 | 1/1986 | Greisch | |
| 4,662,974 | 5/1987 | Roberts | |
| 4,668,472 | 5/1987 | Sakamoto et al. | |
| 4,738,823 | 4/1988 | Englemann | |
| 4,805,280 | 2/1989 | Elander et al. | 29/509 X |
| 4,811,861 | 3/1989 | Roberts | |

Primary Examiner—Joseph M. Gorski
Attorney, Agent, or Firm—Dana M. Schmidt

[57] ABSTRACT

A novel slide test element and method of making are described. Both feature a lip coined in the sidewall of a recess shaped in a frame member to hold the reaction member bearing the detecting reagents. The lip then overhangs the reaction member, once assembled. Assembly occurs by bending the frame member with the lip facing outwardly, thus forcing the lip to part a distance sufficient to allow the reaction member to be inserted. An optional stacking and fusing procedure is also described to facilitate shipment of frame members prior to assembly.

4 Claims, 5 Drawing Sheets

SLIDE FRAME AND MANUFACTURING PROCESS

FIELD OF THE INVENTION

This invention relates to a slide-like test element for use in clinical chemistry and a method for its manufacture.

BACKGROUND OF THE INVENTION

The clinical analysis of biological fluids is most conveniently done using so-called "dried" slide-like test elements which have no wet reagents in liquid form. Prior to this invention, such elements have been manufactured from 3 or 4 separate pieces that have to be assembled and sealed together. U.S. Pat. No. 4,169,751 is illustrative of a useful process, wherein four lock tabs 20–23 are formed in the sidewalls of a recess in one of the pieces of the frame member or holder, and then bent over to lock a reaction member bearing reagents that is inserted into the recess.

Although those test elements and assembly methods have been very useful, the method does involve a number of components specifically manufactured with fairly complex shapes, and assembly using ultrasound. Such a process has to be used carefully to assure adequate bonding. Furthermore, more parts for assembly requires more quality control of the finished product. There has been a need, therefore, to reduce the number of component parts and to simplify the manufacturing procedure.

Still further, the aforesaid process requires either that both the frame member and reaction member be made at the same site prior to assembly, or that if made at separate sites, the pre-formed frame members be shipped to the assembly site. The latter step involves collection of frame members and packaging, which if not done correctly can make reorientation of the frame members difficult during subsequent assembly. That is, a loose, random collection of frame members into a package would necessitate proper reorientation at the assembly site before they can be used. Therefore, there has been a need to improve the packaging of such pre-formed frame members if such have to be shipped.

SUMMARY OF THE INVENTION

We have developed a manufacturing process that solves the above-noted problems, and in the process produces an assembled slide-like test element having novel features.

More specifically, in accord with one aspect of the invention, there is provided a test element for analytical assays of biological liquids, comprising a reaction member including one or more layers on a support, the one or more layers including a reagent, and a frame member for the reaction member, the frame member comprising a base having an aperture generally centered on but smaller in diameter than the dimensions of the reaction member, a recess in the base of dimensions large enough to hold the reaction member so as to overlay the aperture, a lip overhanging the recess and the reaction member in the recess, the lip extending for a majority of the distance around the recess and the reaction member to confine the reaction member in place in the recess, and an exposed groove immediately adjacent to at least a portion of the lip.

In accord with another aspect of the invention, there is provided a method of assemblying a slide-like test element requiring insertion of a reaction member into a pre-formed frame member, the method comprising the steps of a) forming a cold-flowable frame member with an opening therein dimensioned to fit the dimensions of the reaction member; b) forming a reaction member with outside dimensions selected to allow the reaction member to fit within the opening; c) transporting the frame member to a site for assembly with the reaction member; and d) assemblying the reaction member with the frame member. The method is improved in that the step a) comprises the steps of
  i) for each frame member, first forming an aperture passing through the frame member, the aperture being smaller in dimensions than the opening to be formed,
  ii) thereafter forming the opening as a recess in the frame member that is generally centered on and overlies the aperture, with sidewalls;
  iii) and after step ii), cold-flowing at least a portion of the sidewalls to form an overhanging lip that overhangs the opening and is shaped for holding in place a reaction member.

In accord with still another aspect of the invention, there is provided a method of assemblying a slide-like test element requiring insertion of a reaction member into a pre-formed frame member, the method comprising the steps of a) forming a heat-fusible plastic frame member with an opening therein, at one site; b) forming a reaction member with outside dimensions selected to allow the reaction member to fit within the opening, at another site; c) transporting the frame member to a site for assembly with the reaction member; and d) assemblying the reaction member with the frame member. The method is improved in that the method further includes, prior to step c), the steps of stacking together the frame members after step a), and temporarily fusing the members together in the stack by fusing with heat at least a portion of at least one side edge of a frame, to the corresponding side edge of adjacent frames, forming an adhesion stripe; and transporting the stack so fused in step c).

In yet another aspect of the invention, there is provided a method of assemblying a slide-like test element requiring insertion of a reaction member into a pre-formed frame member, the method comprising the steps of a) forming a heat-fusible plastic frame member with an opening therein, at one site; b) forming a reaction member with outside dimensions selected to allow the reaction member to fit within the opening, at another site; c) transporting the frame member to a site for assembly with the reaction member; and d) assemblying the reaction member with the frame member. The method is improved in that the step a) comprises the steps of forming the frame member out of a flexible polymer, and of forming a lip around and projecting out over the opening, and wherein the step d) comprises the step of
  i) bending the frame member to force the lip to pull away from the opening a distance greater than the dimensions of the reaction member;
  ii) inserting the reaction member past the lip and into the opening; and
  iii) relaxing the frame member and the lip so that the lip returns to dimensions that are effective to hold the reaction member in the opening.

Accordingly, it is an advantageous feature of the invention that a method of making a test element is provided that has fewer steps and fewer separate parts to keep track of.

It is a related advantageous feature that the process eliminates the need for ultrasonic bonding.

It is a further related advantageous features that a novel test element results from this method.

Another advantageous feature of the invention is that pre-formed frame members to be used to assemble the test element can be readily packaged and shipped without complicating subsequent assembly.

Other advantageous features of the invention will become apparent upon reference to the following Detailed Description, when read in light of the attached drawings.

DESCRIPTION OF THE PREFERRED EMBODIMENTS

The invention is described hereinafter in connection with its preferred embodiments, wherein a colorimetric test element of a preferred construction is prepared by assemblying a reaction member with reagents, into a flexible frame member of preferably heat-fusible plastic. The assembly steps feature cold-flow formation of the plastic, packaging of the formed plastic by a temporary heat-fusion step, and/or bending of the unpackaged, plastic frame member to insert the reaction member made at a different location.

In addition to such preferred embodiments, the invention is applicable to any test element for analytical assays, regardless of the type of reaction performed by the reaction member, so long as it involves an overlying lip in a frame member having the features set forth hereinafter. Also, the steps of cold-flow member formation and assembly by bending are further applicable whether or not the frame member is of a heat-fusible plastic, and whether or not the preformed frame member is shipped without the reaction member by assemblying a stack of such frame members and temporarily adhering them together. Still further, the assembly methods of the invention are equally applicable when the reaction member is made at the assembly site in previous steps, rather than at a site different from the assembly site.

Slide Test Element Invention

Figures 1, 2:
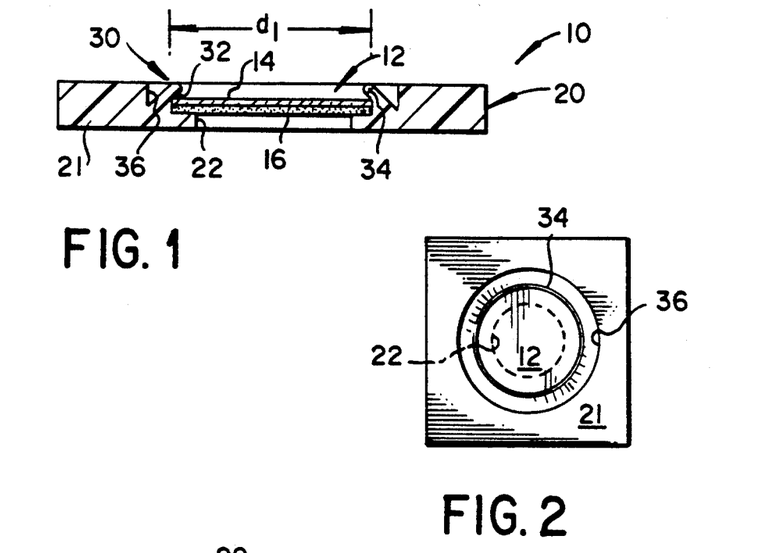
FIG. 1 is an elevational view in section of a test element prepared in accordance with the invention.
FIG. 2 is a top plan view of the test element of FIG. 1.

As shown in FIGS. 1 and 2, a slide test element 10 constructed in accordance with this invention comprises a reaction member 12 and a frame member 20. The reaction member is conventional and comprises a transparent support 14 and thereon at least one layer 16 containing at least one reagent needed to produce a detectable change in response to a targeted analyte in a patient liquid, the change being quantitative in accord with the amount of analyte present. Most preferably, member 12 provides a colorimetric assay, and such are well-known both in the patent literature and the commercial world, e.g. those elements available under the trademark "Ektachem" slides from Eastman Kodak Co. Other conventional elements also feature such a frame member holding a reaction member, for example ion-selective electrode (ISE) elements, which if using an electrode of curved shape, can also be made according to this invention. ISE elements have as their reagent(s), at least an ionophore that selectively associates with and carries the ion of choice across an ion-selective membrane.

Regarding frame member 20, these conventionally comprise a flexible, heat-fusible plastic base 21 of a generally planar shape, having a fluid-metering aperture 22 extending all the way through and means 30 for holding the reaction member in place over aperture 22. Of necessity, aperture 22 is smaller in dimensions than the reaction member that overlies it.

In accordance with one aspect of the invention, holding means 30 preferably comprise a recess 32 in base 21, of dimensions such as diameter "$d_1$" that are large enough to retain reaction member 12, and a lip 34 overhanging that recess and the reaction member, thus holding in place the reaction member. As shown, FIG. 2, lip 34 preferably extends at least the majority of the distance around the circumference of recess 22. As used herein, "majority" means at least 51%. Most preferably, it extends the entire distance around recess 32. Still further, the holding means comprise a groove 36 that is substantially co-extensive with lip 34 simply because it is co-formed with lip 34. Most preferably, the shapes in plan view of lip 34 and groove 36 are that of an annulus. Lip 34 thus defines the viewing aperture of element 10.

Because of the presence of lip 34, no other retaining means is needed to hold reaction member 12 within recess 32.

Alternate embodiments of the slide element are discussed after the "Method of Manufacture".

Method of Manufacturing

Such a slide element is made by a process of 1) forming separately the frame member and the reaction member, 2) optionally stacking together individual frame members for shipment to an assembly site, and then 3) assemblying the reaction member into the frame member. Each of these 3 steps has been improved upon in aspects of the invention, as follows:

1) Forming the Two Components of the Element

The methods of forming the reaction members are known and conventional, and do not comprise any part of this invention. It is the frame member method of formation that is novel, as follows:

In the sequence shown in FIGS. 3A-3E, a single frame member 20 is depicted for clarity as it moves through its various stages shown as 20A, 20B, etc. However, it will be appreciated that the discussion that follows can be applied to a side-by-side array of such individual members temporarily linked together as part of a common, preferably continuous web as shown, for example, in U.S. Pat. No. 4,668,472. After the formation of frame member 20 is complete, FIG. 3E, those connected members are then simply severed at their temporary link.

Figure 3A:
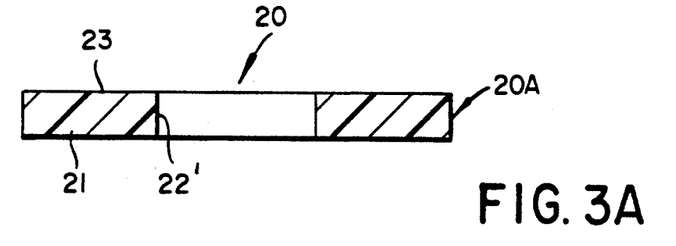
FIGS. 3A–3E are elevational views in section, some fragmentary, illustrating a preferred method of preparing the frame member.
Figure 3B:
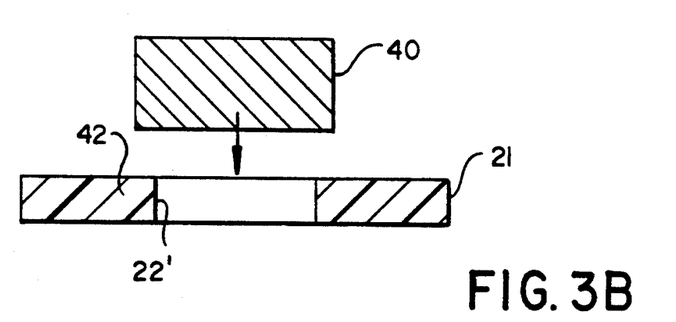
Figure 3C:
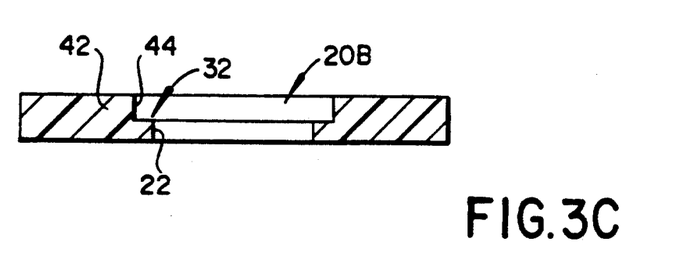

Thus, FIG. 3A, plastic base 21 of frame member 20A has a top surface 23 and is apertured at 22' by a conventional punch, not shown. Thereafter, it is moved to the next station in the process, FIG. 3B, where a punch 40 is brought down to cold-form the upper portion 42 of base 21 to form recess 32 having sidewalls 44. This usually results in a reshaping of aperture 22' so as to shrink it to aperture 22 of a smaller diameter, FIG. 3C. As noted above, recess 32 is aligned with and generally centered on, but larger in dimensions than, aperture 22 of frame member 20B. (The center of recess 32 can be misaligned with the center of aperture 22 as much as 0.05 mm, for example.) Next, FIG. 3D, a specialized punch 50 is brought down to modify sidewalls of recess 32. Staking tool 50 comprises a mandrel cylinder 52 and a concentric, relatively movable forming sleeve 80. Mandrel cylinder 52 has an axis 54 and includes an end portion 56 having outside dimensions machined to fit snugly within recess 44. Spaced up axis 54 from end 56 a distance "$d_2$" is a groove 70 that extends around the circumference of cylinder 52 the same amount as lip 34 is to extend around recess 32. Distance "$d_2$" is selected to ensure that groove 70 falls inside of recess 32, under top surface 23 of base 21, FIG. 3E. When cylinder 52 is in place, it sits loosely within recess 32, ready for movement of sleeve 80. Optionally, cylinder 52 can also include a boss 72 extending downward, FIG. 3D, from end portion 56, with reduced outside dimensions selected to loosely fit within aperture 22, as shown in phantom, FIG. 3E.

Figure 3D:
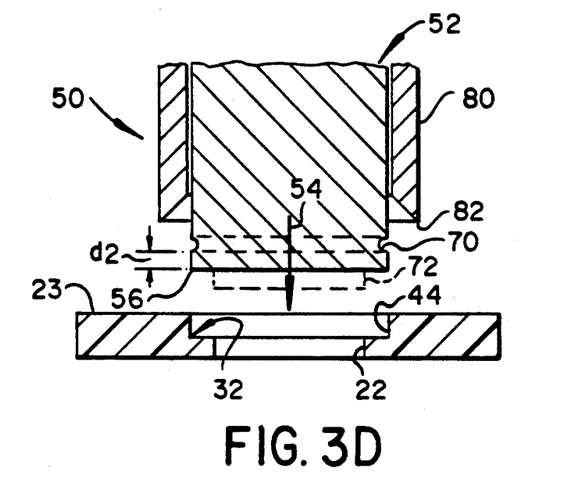
Figure 3E:
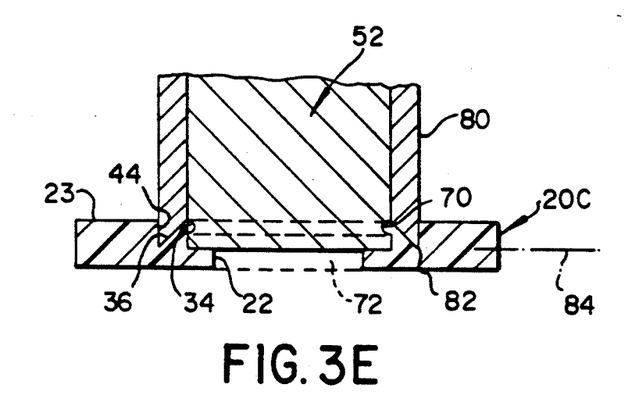

Sleeve 80 is provided with a cutting or staking edge 82 the function of which is to cold-flow or "coin" wall 44 of recess 32 into the lip 34 described above. Groove 70 then functions to assist in the shaping of the lip. The "bite" of edge 82 causes the co-formation of groove 36. Frame member 20C is thus complete, when punch 50 is withdrawn. Most preferably, this is done by removing first sleeve 80, and then cylinder 52, so that end portion 56 can slide past lip 34.

It will be recognized that the frame member so produced, FIG. 3E, is assymmetric when considered about mid-plane 84. Top surface 23 is not a mirror image of the under-surface at which aperture 22 is located.

Figure 4:
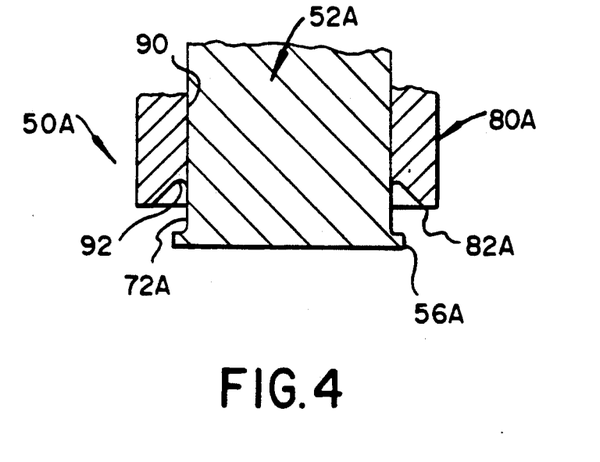
FIG. 4 is an elevational view similar to that of FIG. 3D, but illustrating a staking tool.

Optionally, FIG. 4, the mandrel cylinder can have its lip-forming groove extending for most of the length of the cylinder axis. Parts similar to those previously described bear the same reference numeral to which the distinguishing suffix "A" is appended. Thus, punch 50A comprises cylinder 52A and relatively and separately movable sleeve 80A having a staking edge 82A. End portion 56A of cylinder 52A is also as described before. However, edge 82A is slightly more blunt than before, and groove 70A becomes the outside diameter of cylinder 52A, except for end portion 56A that is dimensioned as before to snugly fit within recess 32 of the frame member. Still further, edge 82A does not extend straight back to inner diameter 90 of sleeve 80A, but rather is rounded off at 92. This rounding of edge 82A acts in concert with end portion 56A to coin out the lip of the frame member, as will be readily appreciated.

At this point, the frame members so produced are ready for assembly, described in detail hereinafter, with reaction members conventionally produced as noted above. This assembly can be done at the site where the finished frame members have just been produced, as a continuation of the assembly process described above.

Optionally, however, and in accord with another aspect of the invention, the produced frame members can be packaged and shipped to an assembly site remote from the site of formation of the frame members. The packaging in such a case needs to be carefully arranged to minimize improper orientation of the frame members. That is, ideally the members should all be shipped so that all of the top surfaces 23 are facing the same direction, due to the element assymmetry produced as noted above.

Figure 5:
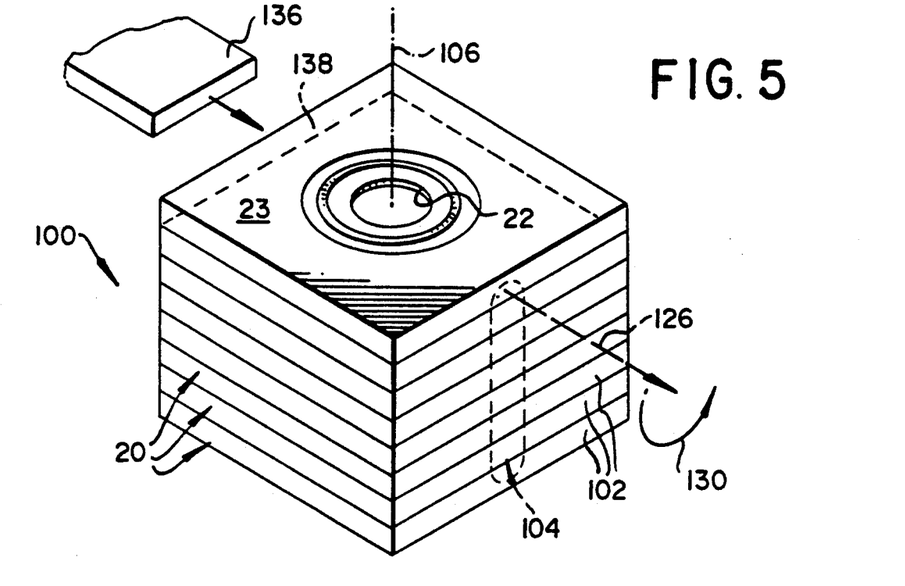
FIG. 5 is a fragmentary isometric view of a package of frame members prepared as in FIGS. 3A–3E, after shipment to an assembly site, illustrating the de-packaging step.

To achieve this end, a stack 100 of the frame members 20 is produced, FIG. 5, in which each member is temporarily fused to adjacent members along at least a portion of one side edge 102 of each, the fusion creating an adhesive stripe 104 that may, or may not, be generally parallel to the axis of symmetry 106 of the stack. Similarly, the stack preferably, but need not, have side edges 102 be directly aligned and coplanar throughout the stack, so that the plane of each frame member may (or may not, respectively) be generally perpendicular to axis 106.

Figure 6:
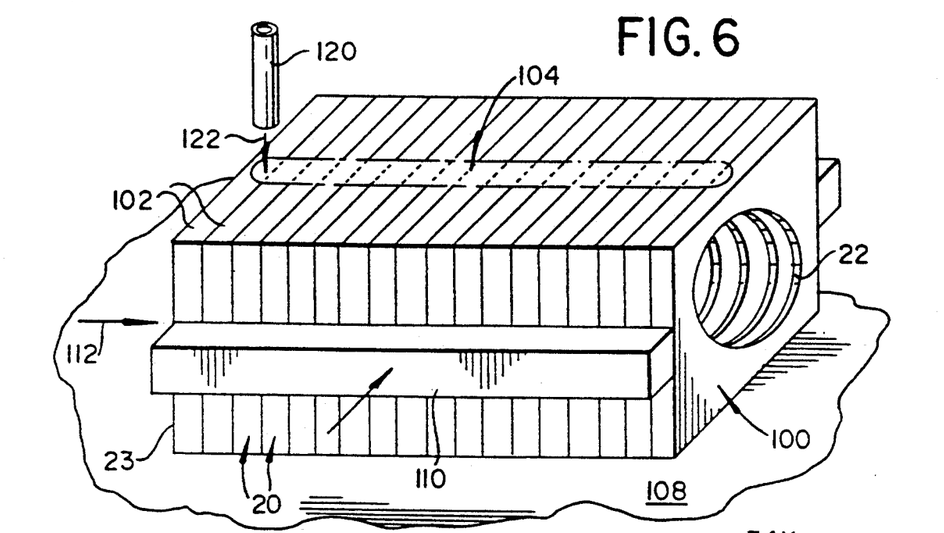
FIG. 6 is a fragmentary isometric view illustrating a method of adhesion of the stack members prior to shipment.

The fusion proceeds as is generally taught by U.S. Pat. Nos. 4,662,974 and 4,811,861, except here applied to frame members 20. This is possible because of the preferable use of heat-fusible plastic as the material of frame members. The preferred process, FIG. 6, is one in which the frame members 20 so produced as described above are aligned in a stack 100 that is oriented against a support 108, preferably between pressurized guide rails 110 to hold the stack together as a force 112 is applied. Most preferably, stack 100 is horizontal at this juncture, although it can be inclined. Aperture 22 can be the advancing side, as shown, or top surface 23 can be the advancing surface. While the frame members 20 so advance, an air gun 120 applies a jet 122 of hot gases (e.g., air) against side edges 102 to form the fusion stripe 104. The temperature of the gas jet should be about 200°-215° C. if frame members 20 are polyethylene, and higher for polystyrene. The pressure of the jet is variable, and a useful pressure includes about 50 cm of water.

Stripe 104 so formed represents a surface phenomenon only, such that substantially no shape deformation occurs at side edges 102. That is, when a frame member is "shucked" from the stack, arrow 126, FIG. 5, it is difficult to detect with the unaided eye where the stripe had been applied—a feature that is important in producing a frame member with generally uniform side edges. Still further, the fusion at the surface only, renders the members readily separatable from the stack, as described below.

The stack 100 is thus suitable for shipment as is, or wrapped in a simple protective bag. Because of the adhesion in the stack, there is no danger members 20 will reorient during shipment.

At the assembly site, the first step in the process, FIG. 5, is to "shuck" off each frame member 20 as needed.

Most preferably, the undersurface of the frame members with aperture 22 exposed, is up. Alternatively, if top surface 23 is up, as shown, when the individual members are removed from the stack, they are flipped over 180°, arrow 130, for reasons that will become apparent.

The "shucking" is achieved by shearing each member 20 to break the adhesion at stripe 104, using a pusher mechanism of some kind, e.g., a pusher blade 136, while holding the stack in place by suitable means (not shown). Stripe 104 is a surface adhesion only, as noted above, such that the shear force that is required is minimal, e.g. about 1–3 kg of force applied to a side edge 138 having a surface area of about 15 mm$^2$.

Figure 7A:
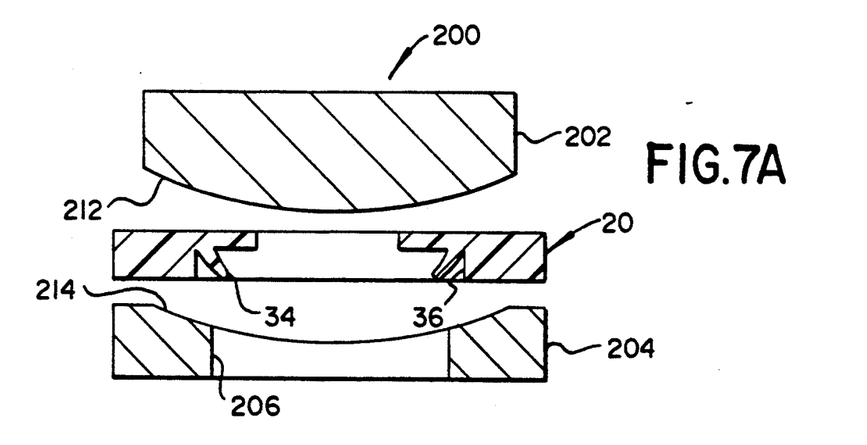
FIGS. 7A–7D are elevational views in section illustrating the process steps of assembly using the frame members prepared in the steps of FIGS. 3A–3E.
Figure 7B:
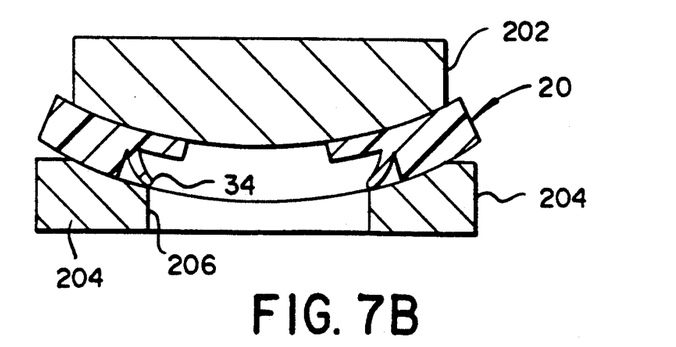

The non-severed frame members are ready for assembly, which optionally proceeds in accordance with yet another aspect of the invention, FIGS. 7A–7D. That is, each frame member 20 in its upside-down orientation, FIG. 7A, is placed within a die 200 having an upper member 202 and a lower member 204, both of which have a generally mating curved surface 212 and 214, respectively. Member 204 is also apertured at 205, with dimensions, e.g., an inside diameter, that are generally between the inside diameter groove 36 and the inside diameter of lip 34. The radii of curvature of surfaces 212 and 214 is selected to bend member 20 as shown in FIG. 7B, sufficiently to "open up" lip 34 to about the dimensions of aperture 206 in lower member 204.

Figure 7C:
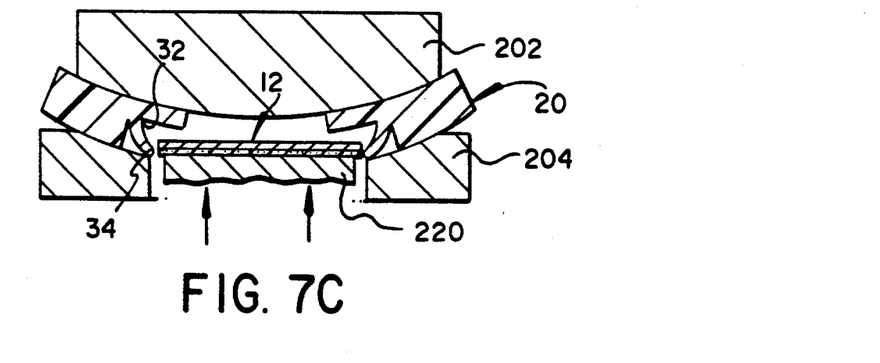
Figure 7D:
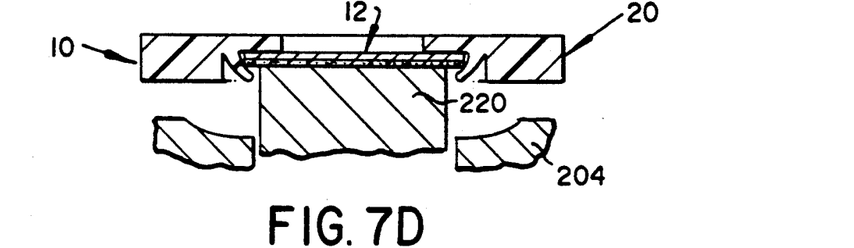

Next, FIG. 7C, a punch 220 of the same or a smaller diameter than that of reaction member 12 and smaller than the inside diameter of aperture 206, is brought up through aperture 206, carrying a reaction member 12 with it, preferably with a liquid-receptive layer up, in contact with punch 220. Preferably, punch 220 is used to punch out individual reaction members 12 from a web. In this manner, reaction member 12 is inserted past lip 34 and into the opening of recess 32.

Next, relative movement is provided between upper member 202 and lower member 204, to allow frame member 20 to straighten out. For example, upper die member 202 can be raised while punch 220 continues pushing upward, and member 202 is raised at a faster rate than punch 220 to effectively relax and straighten out frame member 20 as it lifts off lower member 204, FIG. 7D. (Member 202 is not shown.) As a result, lip 34 closes over reaction member 12, and assembly is essentially complete for slide test element 10. Element 10 is then removed by any convenient apparatus, for packaging.

Lip 34 is effective at this stage to hold member 12 within frame member 20. It is possible, however, for creep to occur during storage, such that lip 34 could pull back into groove 36. To deter this, further processing can be applied, FIGS. 8A and 8B, to further anchor lip 34 in place over reaction member 12. Parts similar to those previously described bear the same reference numeral, to which a distinguishing suffix "X" has been added.

Figure 8A:
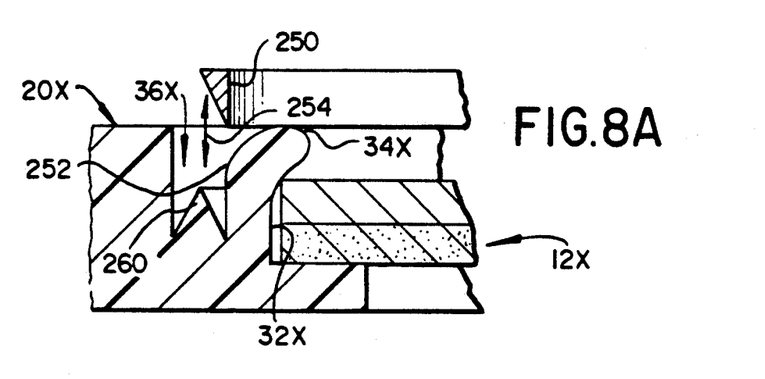
FIGS. 8A and 8B are fragmentary elevational views in section illustrating an optional locking step that further secures the assembly.

Thus, FIG. 8A, frame member 20X holds reaction member 12X in recess 32X via lip 34X, as described above, a groove 36X being left behind as a result of the lip formation. To further stake lip 34X against release of member 12X, a knife edge 250 is aligned with inside surface 252 of groove 36X, preferably all around the circumference of lip 34X. After edge 250 is brought into the groove about ⅛ to ½ of the thickness of frame member 20X, and then withdrawn, arrow 254, it leaves behind a ridge 260 running throughout groove 36X wherever the knife edge contacted the groove. Next, FIG. 8B, a blunt edge 270 is brought down to cold-flow by squashing, ridge 260, leaving a generally flattened surface 272 behind. It is these knifing and squashing steps that further displace material against lip 34X, arrow 274, thus further ensuring its lock against accidental removal of member 12X from the test element.

Figure 8B:
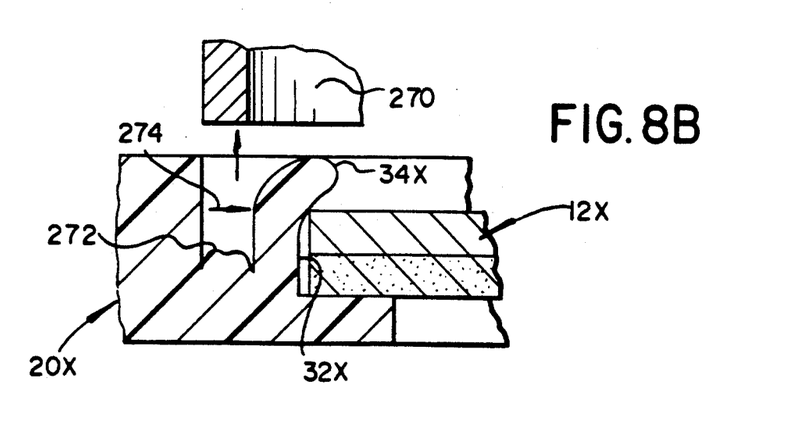
Figure 9:
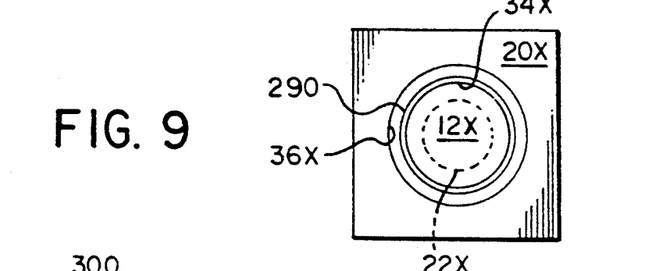
FIG. 9 is a top plan view of an assembled test element finished as shown in FIGS. 8A–8B.

It will be readily apparent that the plan view of slide element 10X so prepared, FIG. 9, is slightly different from that of FIG. 2, due to the creation of additional vertical edge 290 by the process of FIGS. 8A and 8B. As in the case of the element of FIG. 2, aperture 22X is hidden from view and is shown in phantom only.

Figure 10A:
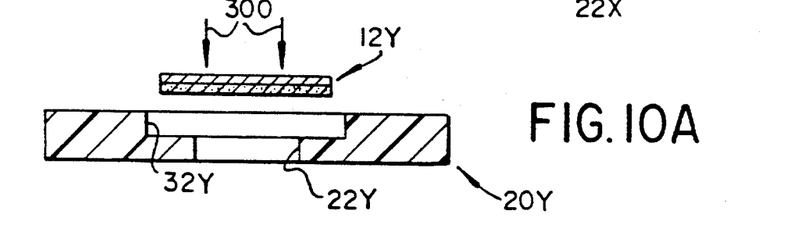
FIGS. 10A and 10B are elevational views similar to those of FIGS. 3A–3E, illustrating another manufacturing process of the invention.
Figure 10B:
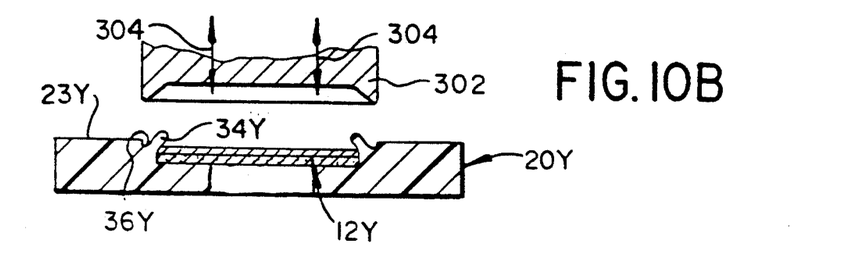

There is yet another method of manufacture that will produce a test element generally as described for FIG. 1. This alternate method is depicted in FIGS. 10A–10B. Parts similar to those previously described bear the same reference numeral, to which the distinguishing suffix "Y" is appended. Thus, FIG. 10A, a frame member 20Y is formed as described above with aperture 22Y and recess 32Y, and reaction member 12Y is also prepared as previously described. However, unlike the previously described method, reaction member 12Y is lowered into recess 32Y, arrows 300. Thereafter, FIG. 10B, a swaging die 302 is lowered and then raised, arrows 304, to cut into top surface 23Y of member 20Y to cold-form lip 34Y, and the corresponding groove 36Y, that extends and overhangs a majority of the circumference of member 12Y, to hold it in.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In a method of assembling a slide-like test element comprising the steps of a) forming a heat-fusible plastic frame member with an opening and a seat at one site; b) forming a reaction member with a diameter selected to allow said reaction member to fit within said opening, at another site; c) transporting said frame member to a site, for assembly with said reaction member; and d) assembling said reaction member with said frame member;

the improvement wherein step a) comprises the steps of forming said frame member out of a flexible polymer, and of forming a lip around and projecting out over said opening, said lip defining an opening having a diameter less than that of said reaction member, and wherein step d) comprises the steps of
 i) bending said frame, thereby enlarging the size of the opening defined by said lip so as to allow said reaction member to pass therethrough;
 ii) inserting said reaction member past said lip and into said opening onto said seat; and
 iii) relaxing said frame member and said lip so that the opening defined by said lip is restored to its original size thereby retaining said reaction member in said opening on said seat.

2. A method as claimed in claim 1 wherein said bending step comprises placing said frame member on a curved surface and applying pressure against said frame member, said curved surface having sufficient curvature to enlarge said opening defined by said lip so as to allow said reaction member to pass therethrough.

3. In a method of manufacturing a slide-like test element comprising a reaction member containing a reagent to produce a detectable change, and a flexible, cold-flowable, heat-fusible plastic frame member holding said reaction member, the method comprising the steps of a) providing said members and b) assembling said members;

the improvement wherein said providing step a) comprises,
- i) for each frame member, first forming an aperture passing through said frame member,
- ii) thereafter forming an opening as a recess in said frame member that is generally centered on and overlies said aperture, such that a seat if formed in said frame member, said opening having sidewalls, said aperture being smaller in diameter than said opening,
- iii) and after step ii), cold-flowing at least a portion of said sidewalls thereby forming an overhanging lip that overhangs said opening and is shaped for holding in place on said seat a reaction member, said lip defining an opening having a diameter less than that of said reaction member, and wherein said assembling step b) comprises the steps of
- iv) bending said frame member, thereby enlarging the size of the opening defined by said lip so as to allow said reaction member to pass therethrough;
- v) inserting said reaction member past said lip and into said opening onto said seat; and
- vi) relaxing said frame member and said lip so that the opening defined by said lip is restored to its original size thereby retaining said reaction member in said opening on said seat.

4. The method of manufacturing as defined in claim 3, and further including between steps a) and b), the steps of:
- c) stacking together frame members produced by said step a),
- d) temporarily fusing the members so stacked together by fusing with heat at least a portion of at least one side edge of a frame member to the corresponding side edge of adjacent frame members, forming an adhesion stripe;
- e) transporting said stack to a location suitable for said step b); and
- f) shearing off individual frame members from said stack at said location to allow said step b) to take place.

* * * * *